United States Patent [19]

DiNinno et al.

[11] Patent Number: 5,034,385

[45] Date of Patent: Jul. 23, 1991

[54] 2-(HETEROARYLSUBSTITUTED)PHENYL CARBAPENEM ANTIBACTERIAL AGENTS

[75] Inventors: Frank P. DiNinno, Old Bridge; Thomas N. Salzmann, North Plainfield; David H. Shih, West Windsor, all of N.J.

[73] Assignee: Merck & Co., Inc., Rahway, N.J.

[21] Appl. No.: 543,939

[22] Filed: Jun. 26, 1990

[51] Int. Cl.[5] .................. C07D 487/04; A61K 31/40
[52] U.S. Cl. ..................................... 514/210; 540/302
[58] Field of Search ......................... 514/210; 540/302

[56] References Cited

U.S. PATENT DOCUMENTS 4,962,101 10/1990 DiNinno ............................. 514/210

Primary Examiner—Robert Gerstl
Attorney, Agent, or Firm—Joseph F. DiPrima; William H. Nicholson

[57] ABSTRACT

Carbapenems having the formula:

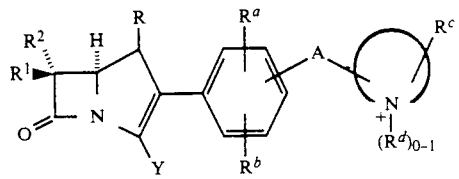

are useful antibacterial agents.

14 Claims, No Drawings

2-(HETEROARYLSUBSTITUTED)PHENYL CARBAPENEM ANTIBACTERIAL AGENTS

BACKGROUND OF THE INVENTION

The present invention relates to antibacterial agents of the carbapenem class, in which the 2-position sidechain is characterized by a phenyl moiety, optionally substituted, to which is attached, usually through an alkyl bridge, a nitrogen-containing heteroaryl group, with attachment being only through a carbon atom of the heteroaryl group, as described in more detail further below.

Thienamycin was an early carbapenem antibacterial agent having a broad spectrum; it has the following formula:

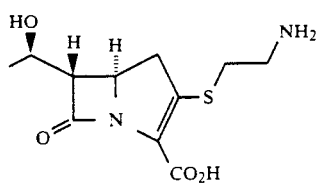

Later, N-formimidoyl thienamycin was discovered; it has the formula:

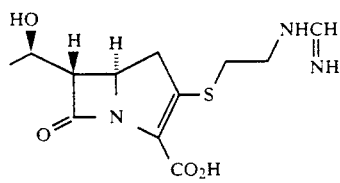

The 2-(heteroarylalkyl)phenyl carbapenems of the present invention have an antibacterial potency equal to or greater than, in most cases, that of either thienamycin or N-formimidoyl thienamycin. The compounds of the present invention are also more resistant than thienamycin or N-formimidoyl thienamycin to degradation by the dehydropeptidase enzyme DHP-I, thus permitting greater therapeutic application of the compounds.

More recently, carbapenem antibacterial agents have been described which have a 2-substituent which is an aryl moiety optionally substituted by, e.g., aminomethyl and substituted aminomethyl. These agents are described in U.S. Pat. Nos. 4,543,257 and 4,260,627 and have the formula:

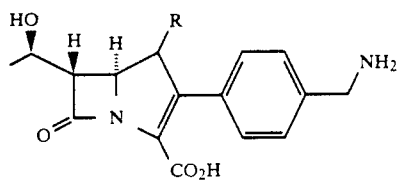

However, these compounds belong to a different class from those of the present invention and are distinguished by different physiological properties.

There is also described in EP-A-0 277 743 a particular class of carbapenems of the formula:

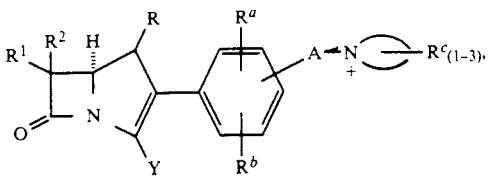

but the disclosure thereof is very limited and none of those compounds suggest the compounds of the present invention.

SUMMARY OF THE INVENTION

The present invention provides novel carbapenem compounds of the formula I:

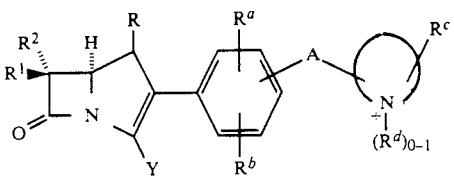

wherein:

R is H or $CH_3$;

$R^1$ and $R^2$ are independently H, $CH_3-$, $CH_3CH_2-$, $(CH_3)_2CH-$, $HOCH_2-$, (R)$-CH_3CH(OH)-$, $(CH_3)_2C(OH)-$, $FCH_2-$, $F_2CH-$, $F_3C-$, (R)$-CH_3CH(F)-$, $CH_3CF_2-$, or $(CH_3)_2C(F)-$;

$R^a$ and $R^b$ are independently hydrogen or:

a) a trifluoromethyl group: $-CF_3$;

b) a halogen atom: $-Br$, $-Cl$, $-F$, or $-I$;

c) $C_1-C_4$ alkoxy radical: $-OC_{1-4}$ alkyl, wherein the alkyl is optionally mono-substituted by $R^q$, where $R^q$ is a member selected from the group consisting of $-OH$, $-OCH_3$, $-CN$, $-C(O)NH_2$, $-OC(O)NH_2$, $CHO$, $-OC(O)N(CH_3)_2$, $-SO_2NH_2$, $-SO_2N(CH_3)_2$, $-SOCH_3$, $-SO_2CH_3$, $-F$, $-CF_3$, $-COOM^a$ (where $M^a$ is hydrogen, alkali metal, methyl or phenyl), tetrazolyl (where the point of attachment is the carbon atom of the tetrazole ring and one of the nitrogen atoms is mono-substituted by $M^a$ as defined above) and $-SO_3M^b$ (where $M^b$ is hydrogen or an alkali metal);

d) a hydroxy group: $-OH$;

e) a carbonyloxy radical: $-O(C=O)R^s$, where $R^s$ is $C_{1-4}$ alkyl or phenyl, each of which is optionally mono-substituted by $R^q$ as defined above;

f) a carbamoyloxy radical: $-O(C=O)N(R^y)R^z$ where $R^y$ and $R^z$ are independently H, $C_{1-4}$ alkyl (optionally mono-substituted by $R^q$ as defined above), together a 3- to 5-membered alkylidene radical to form a ring (optionally substituted with $R^q$ as defined above) or together a 2- to 4-membered alkylidene radical, interrupted by $-O-$, $-S-$, $-S(O)-$, $-S(O)_2-$ or $-NR^e-$, to form a ring (where $R^e$ is hydrogen, $C_1-C_4$alkyl, and $C_1-C_4$alkyl mono-substituted with $R^q$ and the ring is optionally mono-substituted with Rq as defined above);

g) a sulfur radical: $-S(O)_n-R^s$ where $n=0-2$, and $R^s$ is defined above;

h) a sulfamoyl group: —SO$_2$N(R$^y$)R$^z$ where R$^y$ and R$^z$ are as defined above;
i) azido: N$_3$
j) a formamido group: —N(R$^t$)(C=O)H, where R$^t$ is H or C$_{1-4}$ alkyl, and the alkyl thereof is optionally mono-substituted by R$^q$ as defined above;
k) a (C$_1$-C$_4$ alkyl)carbonylamino radical: —N(R$^t$)(C=O)C$_{1-4}$ alkyl, where R$^t$ is as defined above, and the alkyl group is also optionally mono-substituted by R$^q$ as defined above;
l) a (C$_1$-C$_4$ alkoxy) carbonylamino radical: —N(R$^t$)(C=O)OC$_{1-4}$ alkyl, where R$^t$ is as defined above, and the alkyl group is also optionally mono-substituted by R$^q$ as defined above;
m) a ureido group: —N(R$^t$)(C=O)N(R$^y$)R$^z$ where R$^t$, R$^y$ and R$^z$ are as defined above;
n) a sulfonamido group: —N(R$^t$)SO$_2$R$^s$, where R$^s$ and R$^t$ are as defined above;
o) a cyano group: —CN;
p) a formyl or acetalized formyl radical: —(C=O)H or —CH(OCH$_3$)$_2$;
q) (C$_1$-C$_4$ alkyl)carbonyl radical wherein the carbonyl is acetalized: —C(OCH$_3$)$_2$C$_{1-4}$ alkyl, where the alkyl is optionally mono-substituted by R$^q$ as defined above;
r) carbonyl radical: —(C=O)R$^s$, where R$^s$ is as defined above;
s) a hydroximinomethyl radical in which the oxygen or carbon atom is optionally substituted by a C$_1$-C$_4$ alkyl group: —(C=NOR$^z$)R$^y$ where R$^y$ and R$^z$ are as defined above, except they may not be joined together to form a ring;
t) a (C$_1$-C$_4$ alkoxy)carbonyl radical: —(C=O)OC$_{1-4}$ alkyl, where the alkyl is optionally mono-substituted by R$^q$ as defined above;
u) a carbamoyl radical: —(C=O)N(R$^y$)R$^z$ where R$^y$ and R$^z$ are as defined above;
v) an N-hydroxycarbamoyl or N(C$_1$-C$_4$ alkoxy)-carbamoyl radical in which the nitrogen atom may be additionally substituted by a C$_1$-C$_4$ alkyl group: —(C=O)—N(OR$^y$)R$^z$ where R$^y$ and R$^z$ are as defined above, except they may not be joined together to form a ring;
w) a thiocarbamoyl group: —(C=S)N(R$^y$)R$^z$ where R$^y$ and R$^z$ are as defined above;
x) carboxyl: —COOM$^b$, where M$^b$ is as defined above;
y) thiocyanate: —SCN;
z) trifluoromethylthio: —SCF$_3$;
aa) tetrazolyl, where the point of attachment is the carbon atom of the tetrazole ring and one of the nitrogen atoms is mono-substituted by hydrogen, an alkali metal or a C$_1$-C$_4$ alkyl optionally substituted by R$^q$ as defined above;
ab) an anionic function selected from the group consisting of: phosphono [P=O(OM$^b$)$_2$]; alkylphosphono {P=O(OM$^b$)—[O(C$_1$-C$_4$ alkyl)]}; alkylphosphinyl [P=O(OM$^b$)—(C$_1$-C$_4$alkyl)]; phosphoramido [P=O(OM$^b$)N(R$^y$)R$^z$ and P=O(OM$^b$)NHR$^x$]; sulfino (SO$_2$M$^b$); sulfo (SO$_3$M$^b$); acylsulfonamides selected from the structures CONM$^b$SO$_2$R$^x$, CONM$^b$SO$_2$N(R$^y$)R$^z$, SO$_2$NM$^b$CON(R$^y$)R$^z$; and SO$_2$NM$^b$CN, where R$^x$ is phenyl or heteroaryl, where heteroaryl is a monocyclic aromatic hydrocarbon group having 5 or 6 ring atoms, in which a carbon atom is the point of attachment, in which one of the carbon atoms has been replaced by a nitrogen atom, in which one additional carbon atom is optionally replaced by a heteroatom selected from O or S, and in which from 1 to 2 additional carbon atoms are optionally replaced by a nitrogen heteroatom, and where the phenyl and heteroaryl are optionally mono-substituted by R$^q$, as defined above; M$^b$ is as defined above; and R$^y$ and R$^z$ are as defined above;
  ac) C$_5$-C$_7$ cycloalkyl group in which one of the carbon atoms in the ring is replaced by a heteroatom selected from O, S, NH or N(C$_1$-C$_4$ alkyl) and in which one additional carbon atom may be replaced by NH or N(C$_1$-C$_4$ alkyl), and in which at least one carbon atom adjacent to each heteroatom has both of its attached hydrogen atoms replaced by one oxygen thus forming a carbonyl moiety and there are one or two carbonyl moieties present in the ring;
  ad) C$_2$-C$_4$ alkenyl radical, optionally mono-substituted by one of the substituents a) to ac) above and phenyl which is optionally substituted by R$^q$ as defined above;
  ae) C$_2$-C$_4$ alkynyl radical, optionally mono-substituted by one of the substituents a) to ac) above;
  af) C$_1$-C$_4$ alkyl radical;
  ag) C$_1$-C$_4$ alkyl mono-substituted by one of the substituents a)-ac) above;
  ah) a 2-oxazolidinonyl moiety in which the point of attachment is the nitrogen atom of the oxazolidinone ring, the ring oxygen atom is optionally replace by a heteroatom selected from S and NR$^t$ (where R$^t$ is as defined above) and one of the saturated carbon atoms of the oxazolidinone ring is optionally mono-substituted by one of the substituents a) to ag) above;
R$^c$ is R$^a$ as defined hereinabove, hydrogen, or —NR$^y$R$^z$ (where R$^y$ and R$^z$ are defined hereinabove), but independently selected from R$^a$ and from each other if more than one R$^c$ is present, and is attached to a carbon ring atom or a nitrogen heteroatom the valency of which is not satisfied by the ring bonds;
R$^d$ is hydrogen, NH$_2$, O or C$_1$-C$_4$alkyl (where the alkyl group is optionally mono-substituted with R$^q$ as defined under c above);

is a 5- or 6-membered monocyclic aromatic heterocycle or an 8-, 9- or 10-membered bicyclic aromatic heterocycle, the heterocycle containing a first nitrogen in an aromatic 5- or 6-membered first ring, with said first nitrogen quaternary by virtue of a substituent R$^d$ in addition to the ring bonds thereto, with attachment of the heterocycle to A by way of a carbon atom of a ring, with the first ring containing zero or one of either of the atoms of O or S, with the first ring containing zero to two additional nitrogen atoms, with the first ring optionally fused to a 3- or 4-membered moiety to form the optional second ring, with the moiety containing at least one carbon atom, with the moiety containing zero or one of either O or S, with the moiety containing zero to two nitrogen atoms, and with the moiety being saturated or unsaturated and the second ring aromatic or non-aromatic;

A is $(CH_2)_m$—Q—$(CH_2)_n$, where m is zero to 6 and n is zero to 6 and Q is a covalent bond, O, S, SO, $SO_2$, NH, —$SO_2NH$—, —$NHSO_2$—, —CONH—, —NHCO—, —$SO_2N(C_1-C_4alkyl)$—, —$N(C_1-C_4alkyl)SO_2$—, —$CON(C_1-C_4alkyl)$—, —$N(C_1-C_4alkyl)CO$—, —CH=CH—, —CO—, —OC(O)—, —C(O)O— or $N(C_1-C_4alkyl)$; provided when m=n=zero that Q is not a covalent bond;

Y is selected from:
  i) COOH or a pharmaceutically acceptable ester or salt thereof,
  ii) $COOR^3$ wherein $R^3$ is a readily removable carboxyl covering group which is not a pharmaceutically acceptable ester,
  iii) COOM wherein M is an alkali metal, or
  iv) $COO^-$;

provided that when Y is other than iv) and a quaternary nitrogen heteroatom is present, a counterion $Z^-$ is provided.

The $R^a$, $R^b$ and $R^c$ substituents optionally represent from 1 to 3 substituents which may be the same or different and are selected on an independent basis. While a single such substituent is clearly preferred, there is occasion to use up to three such substituents, e.g., where it is desired to enhance the effect of a particular substituent group by employing multiple substituents. Thus, two carboxymethyl substituents may be used. At other times it may be desired to employ a substituent known to enhance antibacterial activity of the overall molecule against a particular bacterium, for example, while also employing a substituent known to improve the duration of action of the overall molecule.

The overall molecule must be electronically balanced. Since a quaternary nitrogen may be present in the compounds of the present invention, a balancing anion must, in that case, also be present. This is usually accomplished by having Y be $COO^-$. However, where Y is, e.g., a pharmaceutically acceptable ester, and a quaternary nitrogen is present, a counterion (anion) $Z^-$ must be provided, or alternatively, an anionic substituent might be utilized. Further, it is within the scope of this invention to utilize an anionic substituent where the quaternary nitrogen is already balanced by $Y=COO^-$. In that case, it will be understood that it is necessary to provide a counterion (cation) for the anionic substituent. However, it is well within the skill of a medicinal chemist, to whom there is available many suitable anionic and cationic counterions, to make such choices.

With reference to the above definitions, "alkyl" means a straight or branched chain aliphatic hydrocarbon radical.

The term "heteroatom" means N, S, or O, selected on an independent basis.

Under the definition of "Y", the term "pharmaceutically acceptable ester or salt" refers to those salt and ester forms of the compounds of the present invention which would be apparent to the pharmaceutical chemist, i.e., those which are non-toxic and which would favorably affect the pharmacokinetic properties of said compounds, their palatability, absorption, distribution, metabolism and excretion. Other factors, more practical in nature, which are also important in the selection, are cost of raw materials, ease of crystallization, yield, stability, hygroscopicity, and flowability of the resulting bulk drug. Since the compounds of the present invention may be carboxylates, the salts would be cations such as benzathine, chloroprocaine, choline, diethanolamine, meglumine and procaine. The metallic cations such as aluminum, calcium, lithium, magnesium and zinc are potential choices. The alkali metal cations sodium and potassium are specifically defined. It will also be noted that the compounds of the present invention are potentially internal salts or zwitterions, since under physiological conditions the carboxyl group may be anionic, and this electronic charge might then be balanced off internally against the cationic charge of a quaternary nitrogen atom. Where this is not the case, and a quaternary nitrogen heteroatom is present, it is provided in the definition of "Y" that a counterion "$Z^-$" is present. This counterion is selected from the group of suitable pharmaceutical anions, e.g., chloride, phosphate and tartrate.

The term "readily removable carboxyl covering group" means a conventional substituent which takes the place of the acidic hydrogen of the carboxyl group and thereby prevents said group from reacting with any of the reagents employed in the various steps of the overall synthesis. Such covering of the carboxyl group is often necessary to prevent unwanted competing reactions involving said carboxyl group from taking place. Thus, all of these compounds are intermediates. The conventional covering substituent must also be "readily removable", by which is meant that it is selectively removable, i.e., it is not likely to be removed during the course of ordinary procedures which are to be carried out on the carbapenem nucleus and sidechains, while, on the other hand, it is likely to be removed by procedures which are not so harsh as to disturb the basic ring structure of the carbapenem nucleus or unprotected substituents thereon.

It is preferred that when one of $R^1$ or $R^2$ is H, the other is (R)—$CH_3CH(OH)$— or (R)—$CH_3CH(F)$—, and (R)—$CH_3CH(OH)$— is most preferred. Further, it is preferred that the configuration at C-6 is (S), and that at C-5 is (R).

Representative A groups are —$CH_2$—, —$CH_2CH_2$—, —$CH_2$—$N(CH_3)$—, —$CH_2$—S—, —$CH_2$—S—$CH_2$—, and —$CH_2O(C=O)$—.

Representative $R^c$ groups are —$CH_3$, —$CH_2CH_3$, —$(CH_2)_3CH_3$, —$OCH_3$, —$SCH_3$,

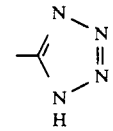

—COOH, —$NHCH_2COOH$, —OH, —$CH_2OH$, —$CH_2COOH$, —$CH_2CH_2COOH$, —$CH_2CONH_2$, —$CH_2CH_2S^+(CH_3)_2$, —$CH_2CH_2SO_3H$,

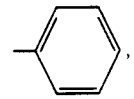

—$CONH_2$, —$SO_2NH_2$, —$SO_3H$, —$NH_2$, —$N(CH_3)_2$, —$CON(CH_3)_2$, —$NHCH_3$, —$CH_2NH_2$, —CN, —$CH_2CN$, —$CH_2SCH_3$, —$CH_2SO_3$,

—CH₂SOCH₃, —CH₂SO₂CH₃, —SO₂CH₃, —SOCH₃, —CH₂OCH₃,
—CH₂P(O)(OH)OCH₃, —CF₃, —CH₂OC(O)NH₂, —CH₂SO₂NH₂,
—SCH₂CH₂CN, Br, Cl, F, —SCF3, —CH₂SCF₃, and —SCH₂CF₃.

The aromatic heterocycle moiety has been conveniently represented throughout by the following formula:

Useful examples of the nitrogen-containing aromatic heterocycle moiety are set out below.

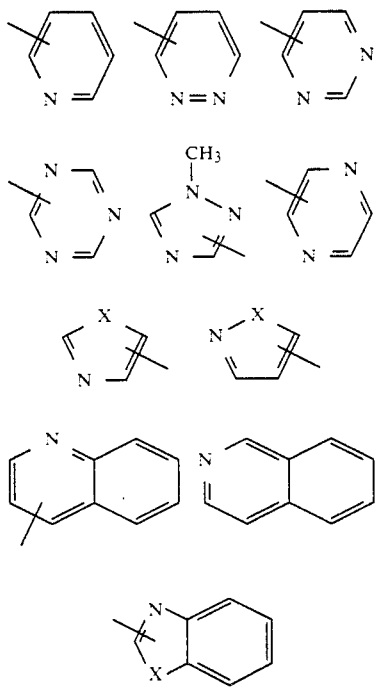

where X=O, S, or NR_e;
R_e=Me, CH₂CN, CH₂CONH₂, CH₂CO₂⁻, CH₂SO₃⁻.

The pyridyl group is preferred since it provides the desired properties of good antibacterial spectrum and potency combined with chemical stability and satisfactory resistance to hydrolysis by the dihydropeptidase (DHP-I) enzyme, together with ready availability and ease of handling as a starting material. However, any of the other groups set out above, as well as those falling within the definition of the heteroaryl moiety set out herein but not specifically described above, are also suitable, although perhaps in some cases less desirable in terms of one or more of the criteria mentioned above. With regard to all of the preferred substituents described above, the following compounds are preferred embodiments of the present invention:

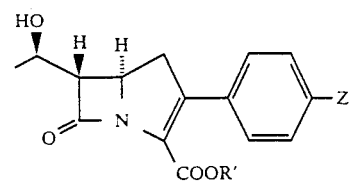

Where Z is:

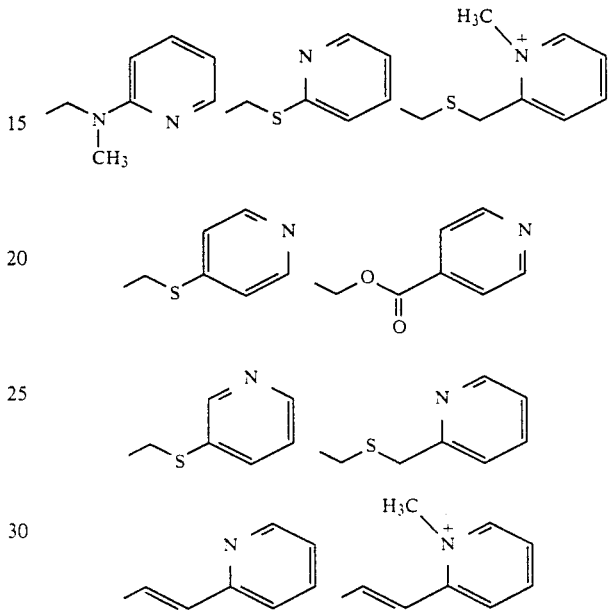

where R' is a negative charge — or an alkali metal salt, a pharmaceutically acceptable carboxy covering group, or additionally a readily removable carboxyl covering group which is not a pharmaceutically acceptable carboxy covering group.

The carbapenem compounds of the present invention are useful per se and in their pharmaceutically acceptable salt and ester forms in the treatment of bacterial infections in animal and human subjects. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel carbapenem compounds of the present invention.

The pharmaceutically acceptable salts referred to above include non-toxic acid addition salts. The Formula I compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

The pharmaceutically acceptable esters of the novel carbapenem compounds of the present invention are such as would be readily apparent to a medicinal chemist, and include, for example, those described in detail in U.S. Pat. No. 4,309,438, Column 9, line 61 to Column 12, line 51, which is incorporated herein by reference. Included within such pharmaceutically acceptable esters are those which are hydrolyzed under physiological conditions, such as pivaloyloxymethyl, acetoxymethyl, phthalidyl, indanyl and methoxymethyl, and those described in detail in U.S. Pat. No. 4,479,947, which is incorporated herein by reference.

The novel carbapenem compounds of the present invention may also take the form where Y is $COOR^3$, where $R^3$ is a readily removable carboxyl protecting group. Such conventional blocking groups consist of known ester groups which are used to protectively block the carboxyl group during the synthesis procedures described further below. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing agents under mild conditions, and catalytic hydrogenation. Examples of such ester protecting groups include benzhydryl, p-nitrobenzyl, 2-naphthylmethyl, allyl, benzyl, trichloroethyl, silyl such as trimethylsilyl, phenacyl, p-methoxybenzyl, acetonyl, o-nitrobenzyl, 4-pyridylmethyl, and $C_1$-$C_6$ alkyl such as methyl, ethyl or t-butyl.

The compounds of the present invention are valuable antibacterial agents active against various Gram-positive and to a lesser extent Gram-negative bacteria and accordingly find utility in human and veterinary medicine. The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy or inhibit the growth of harmful bacteria on medical and dental equipment and as bactericides in industrial applications, for example in waterbased paints and in the white water of paper mills to inhibit the growth of harmful bacteria.

The compounds of this invention may be used in any of a variety of pharmaceutical preparations. They may be employed in capsule, powder form, in liquid solution, or in suspension. They may be administered by a variety of means; those of principal interest include: topically or parenterally by injection (intravenously or intramuscularly).

Compositions for injection, a preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water. Topical applications may be formulated in hydrophobic or hydrophilic bases as ointments, creams, lotions, paints, or powders.

The dosage to be administered depends to a large extent upon the condition and size of the subject being treated as well as the route and frequency of administration, the parenteral route by injection being preferred for generalized infections. Such matters, however, are left to the routine discretion of the therapist according to principles of treatment well known in the antibacterial art. Another factor influencing the precise dosage regimen, apart from the nature of the infection and peculiar identity of the individual being treated, is the molecular weight of the chosen species of this invention.

The compositions for human delivery per unit dosage, whether liquid or solid, may contain from 0.1% to 99% of active material, the preferred range being from about 10-60%. The composition will generally contain from about 15 mg to about 1500 mg of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution.

The preferred method of administration of the Formula I antibacterial compounds is parenteral by i.v. infusion, i.v. bolus, or i.m. injection.

For adults, 5-50 mg of Formula I antibacterial compounds per kg of body weight given 2, 3, or 4 times per day is preferred. Preferred dosage is 250 mg to 1000 mg of the Formula I antibacterial given two (b.i.d.) three (t.i.d.) or four (q.i.d.) times per day. More specifically, for mild infections a dose of 250 mg t.i.d. or q.i.d. is recommended. For moderate infections against highly susceptible gram positive organisms a dose of 500 mg t.i.d. or q.i.d. is recommended. For severe, life-threatening infections against organisms at the upper limits of sensitivity to the antibiotic, a dose of 1000 mg t.i.d. or q.i.d. is recommended.

For children, a dose of 5-25 mg/kg of body weight given 2, 3, or 4 timer per day is preferred; a dose of 10 mg/kg t.i.d. or q.i.d. is usually recommended.

Antibacterial compounds of Formula I are of the broad class known as carbapenems or 1-carbadethiapenems. Naturally occuring carbapenems are susceptible to attack by a renal enzyme known as dehydropeptidase (DHP). This attack or degradation may reduce the efficacy of the carbapenem antibacterial agent. The compounds of the present invention, on the other hand, are significantly less subject to such attack, and therefore may not require the use of a DHP inhibitor. However, such use is optional and contemplated to be part of the present invention. Inhibitors of DHP and their use with carbapenem antibacterial agents are disclosed in the prior art [see European Patent Applications No. 79102616.4 filed July 24, 1979 (Patent No. 0 007 614); and No. 82107174.3, filed Aug. 9, 1982 (Publication No. 0 072 014)].

The compounds of the present invention may, where DHP inhibition is desired or necessary, be combined or used with the appropriate DHP inhibitor as described in the aforesaid patents and published application. Thus, to the extent that the cited European patent applications 1.) define the procedure for determining DHP susceptibility of the present carbapenems and 2.) disclose suitable inhibitors, combination compositions and methods of treatment, they are incorporated herein by reference. A preferred weight ratio of Formula I compound: DHP inhibitor in the combination compositions is about 1:1. A preferred DHP inhibitor is 7-(L-2-amino-2-carboxyethylthio)-2-(2,2-dimethylcyclopropanecarboxamide)-2-heptenoic acid or a useful salt thereof.

DETAILED DESCRIPTION OF THE INVENTION

The 2-(heteroarylalkyl)phenyl carbapenem compounds of the present invention may be prepared in accordance with well known procedures in the art. Particularly useful are the following synthetic schemes in which the symbols R, $R^1$, $R^2$, $R^a$, $R^b$, $R^c$, $R^d$, $R^e$, A, and 

are as defined above.

Scheme A shows the synthetic steps leading to the intermediate A5. A benzene moiety, optionally substituted with $R^a$, $R^b$ or suitable precursor substituents thereof, may be added to azetidin-2-one A1 in a Grignard reaction. The Grignard reaction requires that the Grignard reagent A2 be prepared by reaction of the corresponding bromobenzene derivative and magnesium with 1,2-dibromoethane initiation in a suitable polar aprotic solvent, such as THF, diethyl ether, or the like, from 20° C. to 60° C., and subsequently contacting the Grignard reagent (A2) with A1 in a suitable polar aprotic solvent, such as THF, diethyl ether, or the like, at form −70° C. to about 20° C. to produce azetidin-2-one A3. Alternatively, the bromobenzene may be reacted with t-butyllithium, n-butyllithium, or the like in a suitable polar aprotic solvent, such as THF, diethyl ether, or the like, at from −78° to −50° C. followed by the addition of magnesium bromide to produce the same Grignard reagent A2. $R^i$ of A1 is in practice pyrid-2-yl but may clearly be a variety of substituents including aromatic and heteroaromatic substituents. Further $R^i$ might be for example phenyl, 2-pyrimidinyl or 2-thiazolyl.

Azetidin-2-one A3 is an intermediate that may be ring closed to a carbapenem. It is on this intermediate that $R^a$, $R^b$ or precursor substituent such as t-butyldimethylsilyloxy-methyl may be modified where such modification is incompatible with the carbapenem nucleus. For example, a convenient reaction to remove the t-butyldimethylsilyl group of A3 is to expose it to a 2% solution of sulfuric acid in methanol at 0° C. for from a few minutes to several hours. Flow Sheet B shows the resulting compound A4. If a t-butyldimethylsilyl group was removed by exposing carbapenem A5 to tetra-n-butylammonium fluroide and acetic acid in THF, a substantial portion of carbapenem would be degraded and lost. Thus, modification of the precursor substituent in this instance and replacement with another precursor substituent or even -A-heterocycle is optionally performed before the intramolecular cyclization is carried out, provided the substituent is uncharged.

Compound A3 or A4 may be ring closed to carbapenem A5 by refluxing in xylene with a trace of p-hydroquinone for about 1 to 2 hours in an inert atmosphere. It is on this intermediate A5 that final elaboration to generate the -A-heterocycle moiety from a precursor substituent, e.g. hydroxymethyl, may be accomplished, as will be described in detail hereinbelow. Removal of the protecting groups by methods known in the art, such as a palladium (0) catalyzed deallylation, then provides the final compound Formula I. Such final elaboration and deprotection is described in further detail below.

FLOW SHEET A

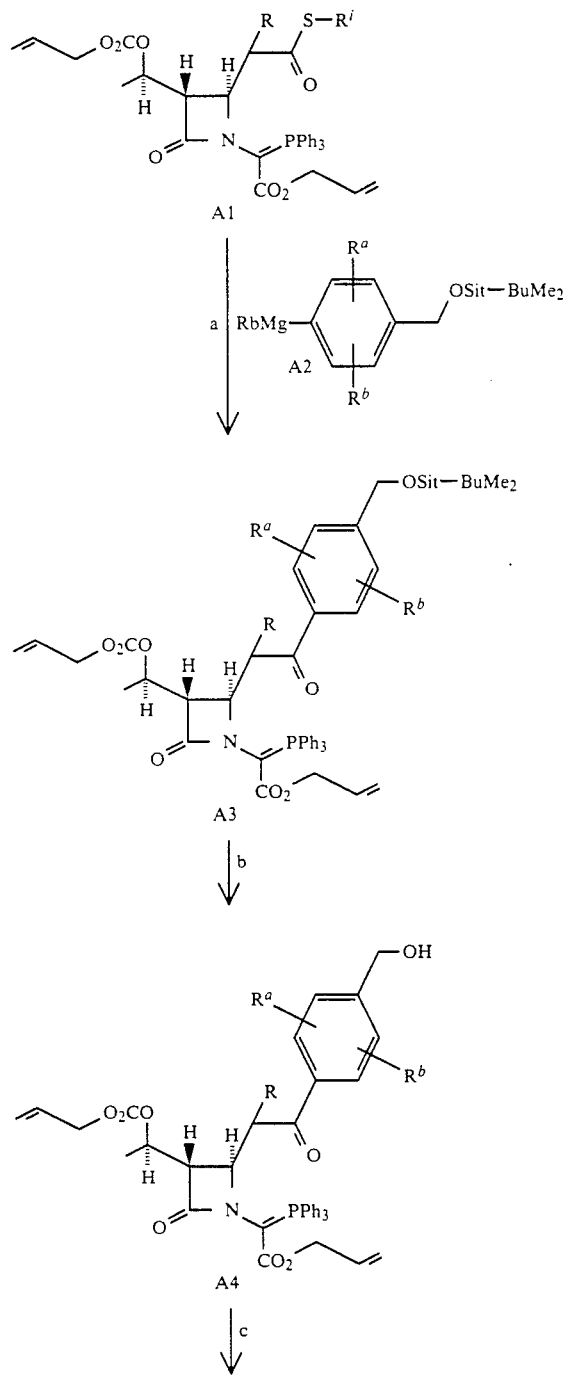

-continued
FLOW SHEET A

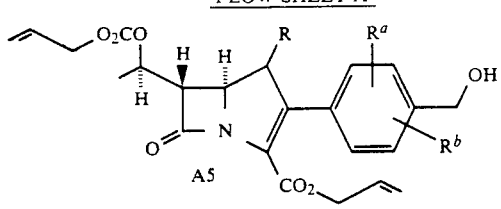

a. THF
b. H₂SO₄/MeOH
c. xylenes, 145° C.

stannane B3. A metal halide, such as lithium chloride, zinc chloride and the like, is added and the reaction solution is quickly warmed to a suitable temperature, such as 0° to 50° C., and allowed to stir for a suitable amount of time. The carbapenem B4 is obtained by conventional isolation/purification methodology known in the art. Final elaboration of the -A-heterocycle moiety from a precursor substituent, e.g. hydroxymethyl, may be accomplished on carbapenem intermediate B4. Removal of protecting groups then provides the final compound of Formula I. Such final elaboration and deprotection is described in further detail below.

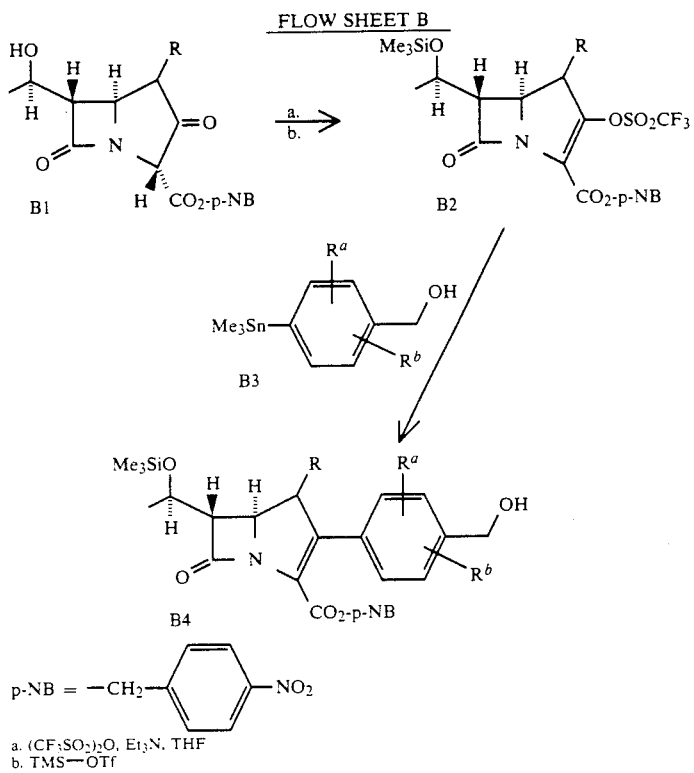

Flow Sheet B shows an alternative synthesis of an intermediate functionally equivalent to A5, i.e. attachment of the base benzene to the 2-position of the carbapenem. This synthesis involves a palladium catalysed cross-coupling reaction between a carbapenem triflate and a suitably substituted arylstannane, a process which is described in U.S. Pat. Appl. No. 485,096 filed Feb. 26, 1990. Thus the 2-oxocarbapenem B1 is reacted with a suitable trifluoromethanesulfonyl source, such as trifluoromethanesulfonic anhydride, trifluoromethanesulfonyl chloride and the like, in the presence of an organic nitrogen base, such as triethylamine, diisopropylamine and the like, in a polar aprotic solvent, such as methylene chloride or tetrahydrofuran. An organic nitrogen base, such as triethylamine and the like, is then added to the reaction solution followed immediately by a silylating agent, such as trimethylsilyl trifluoromethanesulfonate to provide intermediate B2. An aprotic polar coordinating solvent, such as DMF, 1-methyl-2-pyrrolidinone and the like, is added. This is followed by the addition of a palladium compound, such as tris(dibenzylidene-acetone)dipalladium-chloroform, palladium acetate and the like, a suitably substituted phenylphosphine, such as tris(4-methoxyphenyl)phosphine, tris(2, 4, 6-trimethoxyphenyl)phosphine and the like, and the Azetidin-2-one A1 ($R^i$=2-pyridyl), a pyridyl-thioester, is a well known compound in the production of carbapenems. Diverse synthetic schemes useful to make A1 may be imagined by the skilled artisan. Particularly useful to the instant invention is a synthetic scheme set out further in Flow Sheet C below in which the symbol $R^i$ is as defined above. The steps for preparing intermediate A1 are analogous to the procedures described, for example, in U.S. Pat. Nos. 4,260,627 and 4,543,257; L. D. Cama et al., Tetrahedron, 39, 2531 (1983); R. N. Guthikonda et al., J. Med. Chem., 30, 871 (1987).

FLOW SHEET C

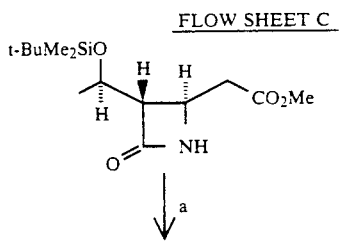

-continued
FLOW SHEET C

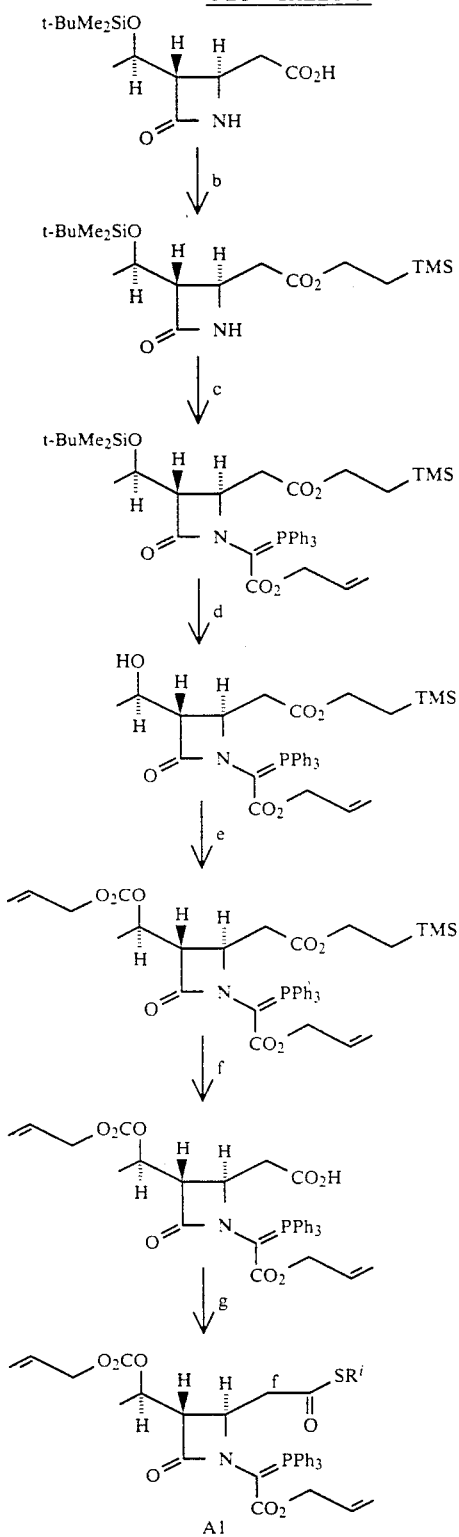

a. NaOH/MeOH b. carbonyl diimidazole
   HO⌒TMS c. OHCCO₂⌒;
   SOCl₂;
   Ph₃P d. 6N HCl/MeOH e. ClCO₂⌒⌒. DMAP f. nBu₄NF g. R$^i$—SS—R$^i$, Ph₃P The R$^c$ substituents herein are intended to represent suitable further substituents on the heterocycle moiety. As seen above, the heterocycle moieties are monocyclic or bicyclic aromatic groups containing heteroatoms. Given this class of primary substituent, further suitable substituents may be readily discovered in the penem and carbapenem art. For example, suitable substituents for heterocycle moieties are generally taught in U.S. Pat. No. 4,729,993 assigned to Merck and Co. or in U.S. Pat. No. 4,746,736 assigned to Bristol-Myers Co.

Broadly, R$^c$ may be the same or different and may be selected on an independent basis from the group as defined above. While a single such substitution is preferred, there is occasion to use up to two such substituents on a heterocycle moiety, where it is desired to enhance the effect of a particular substituent group by employing multiple substituents. The particular choice of R$^c$ will depend upon the situation. For instance, a specific R$^c$ may lend particular stability to a nitrogen cation. At other times it may be desired to employ a substituent known to enhance antibacterial activity of the overall molecule against a particular bacterium, for example, while also employing a substituent known to improve some other property such as water solubility of the duration of action of the overall molecule.

The scope of R$^c$ herein includes two specific types of further substituent attached to the heterocycle moiety. A first type of R$^c$ are those attached to a ring carbon and a second type of R$^c$ are those attached to a neutral ring nitrogen. Persons skilled in the art will readily recognize that a wide range of organic substituents are suitably used as R$^c$. Persons skilled in the art will also recognize that some substituents including the —NR$^y$R$^z$ substituents, useful for one purpose of R$^c$, i.e. carbon substitution, are not equally useful in the other, i.e. nitrogen substitution.

Preferred R$^c$ attached to ring carbon atoms are —NH₂, —SCH₃, —SOCH₃, —CH₂OH, —(CH₂)₂OH, —OCH₃, —COOM$^b$, —CH₂COOM$^b$, —CH₂CH₂COOM$^b$, —CH₂SOCH₃, —CH₂SCH₃, —SO₃M$^b$, —CH₂SO₃M$^b$, —CH₂CH₂SO₃M$^b$, —Br, —Cl, —F, —I, —CH₃, CH₂CH₃, CH₂CONH₂ and CH₂CON(C₁-C₄alkyl) where M$^b$ is defined above. Preferred R$^c$ attached to neutral ring nitrogen atoms are —CH₂OH, —(CH₂)₂OH, —CH₂COOM$^b$, —CH₂CH₂COOM$^b$, —CH₂SOCH₃, —CH₂SCH₃, —CH₂SO₃M$^b$, —CH₂CH₂SO₃M$^b$, —CH₃, CH₂CH₃, CH₂CONH₂ and CH₂CON(C₁-C₄alkyl) where M$^b$ is defined above.

It is preferred that each heterocycle moiety have no more than two R$^c$ substituents which are other than hydrogen. The previously listed more specific structures should be interpreted to have no more than two R$^c$ for each monocyclic group.

The scope of R$^d$ includes a single type of further substituent attached to a heterocycle moiety. The R$^d$ substituents are attached to a cationic nitrogen which is aromatic. Preferred $R^d$ attached to cationic nitrogen atoms are hydrogen, —CH$_3$, CH$_2$CH$_3$, —CH$_2$CH$_2$CH$_3$, —CH$_2$COOM$^b$, —CH$_2$SO$_3$M$^b$, —NH$_2$ and O$^{(-)}$, where M$^b$ is defined above.

The general formula I is intended to encompass alternative charged and uncharged states for the heterocycle substituents. It is understood that certain of those substituents may be cationic by virtue of having a quaternizing hydrogen atom attached to the nitrogen, or may exist or be produced as a neutral substituent by virtue of the absence of such a hydrogen atom (i.e. when there is no R$^d$). Various factors determine whether such a substituent will be predominately cationic or neutral in a given physical state. The particular ratio of neutral form to cationic form will depend upon the basicity of the amine and acidity of a solution. When such a substituent is in a protonated quaternized state, the compound exists as a zwitterion which is internally balance as to charge or as an ammonium salt which is externally balanced. In illustration, if there is no R$^d$ present, it is understood that such a substituent is neutral (there is no positive charge on the nitrogen). A compound containing such a substituent is typically produced in this form as a salt, wherein M is an alkali metal, and may exist in solution in its neutral form. However, depending upon conditions, a compound containing a neutral type Ib substituent may be in equilibrium with, and may also be represented by a formula showing, the corresponding compound containing the quaternized protonated substituent where R$^d$ is present and is a hydrogen atom. Furthermore the same compound may exist with the heterocycle substituent in a completely protonated quaternized form, for instance in an aqueous solution in the presence of a stoichiometric amount of a strong mineral acid. It is intended herein that both the protonated and the neutral forms of heteocycle substituents are within the scope of the present invention.

Suitable A spacer moieties include —CH$_2$—, —CH$_2$CH$_2$—, —CH$_2$CH$_2$CH$_2$—, —CH$_2$CH$_2$CH$_2$CH$_2$—, —OCH$_2$CH$_2$—, —SOCH$_2$—, —SO$_2$CH$_2$—, —SCH$_2$CH$_2$—, —SOCH$_2$CH$_2$—, —SO$_2$CH$_2$CH$_2$—, —NHCH$_2$CH$_2$—, —N(CH$_3$)CH$_2$CH$_2$—, —CH$_2$N(CH$_3$)CH$_2$CH$_2$—, —CONHCH$_2$CH$_2$—, —SO$_2$NHCH$_2$CH$_2$—, —COCH$_2$—, —CH=CHCH$_2$— and —CH$_2$OCH$_2$CH$_2$—. Preferably, where Q is O, S, NH or N(C$_{1-4}$alkyl), then n is 2-6 and m is as previously described.

The cationic heterocycle moieties are prepared by quaternization of an aromatic ring nitrogen of a neutral precursor substituent on the benzene ring. Examples of neutral precursor substituents are —CH=CH—(2-pyridyl), —CH$_2$OC(O)—(4-pyridyl) or —CH$_2$S—(4-pyridyl). Quaternization is accomplished by reacting the nitrogen compound in an inert organic solvent (e.g. CH$_2$Cl$_2$) at about 0° C. to room temperature with an alkylating agent R$^d$—Y where R$^d$ is given above and Y is a leaving group such as iodide, bromide, mesylate (methanesulfonate), tosylate (p-toluenesulfonate) or triflate (trifluoromethanesulfonate). Alternatively, the aromatic ring nitrogen may be quaternized by reaction with an oxidizing agent such as 3-chloroperbenzoic acid (giving the N-oxide) or an aminating reagent such as o-(2,4,6-triisopropylbenzenesulfonyl)hydroxylamine (giving the N-amino derivative) in a suitable solvent (e.g. dichloromethane or CH$_3$CN) at about room temperature. In addition, the neutral precursor moiety may be rendered cationic through protonation of the basic aromatic ring nitrogen. This may be accomplished by treatment of the neutral precursor with a suitable inorganic or organic acid, e.g. hydrochloric acid, phosphoric acid, hydrobromic acid, acetic acid or benzoic acid. Protonation may further be accomplished by a carboxylic acid function elsewhere in the molecule, including the C-3 carboxyl on the carbapenem.

The neutral precursor moiety may be already attached to the benzene ring at the time of its connection to the carbapenem. However, the neutral precursor moieties are generally added to the benzene following attachment of the benzene to the carbapenem. Conveniently, the benzene side-chain should be synthesized with a precusor substituent which may be elaborated into the desired cationic substituent. The identity of the precursor substituent will vary according to the particular R$^a$ desired. For example, one such precursor substituent is hydroxymethyl.

The hydroxymethyl precursor substituent may be elaborated into the -A-heterocycle moieties by converting the hydroxyl into an active leaving group such as an iodide followed by reaction with a desired nitrogen containing aromatic compound. More particularly, two alternative procedures may be utilized to produce a leaving group on the precursor to moiety -A-heterocycle and subsequently to replace such a leaving group with moieties of the type just described.

For a first procedure, the hydroxyl group of the precursor substituent may be converted to a methanesulfonate group by treating with methanesulfonyl chloride in the presence of triethylamine. A suitable solvent, e.g., dichloromethane, is employed and the reaction is carried out at reduced temperatures. In turn, the methanesulfonate intermediate may converted to the reactive iodide derivative by treatment with sodium iodide in a suitable solvent, e.g., acetone, at reduced or ambient temperatures. Alternatively, the hydroxyl group may be directly converted into the iodide group by common methods known to the art. For example, treatment of the hydroxyl group with methyl triphenoxyphosphonium iodide in a suitable solvent, such as dimethylformamide, at reduced or ambient temperatures, directly provides the desired iodide. The iodide is then reacted in a nucleophilic displacement reaction with an aromatic compound which has a nucleophilic side-chain substituent such as mercapto or amino. In this displacement reaction, it is the side-chain substituent that is the reacting nucleophile and not the aromatic ring nitrogen. Suitable substrates for this reaction include 2-(mercaptomethyl)pyridine, 2-aminopyridine, 2-(aminomethyl)-pyridine or 4-(mercaptomethyl)pyridine. The reaction is carried-out in an inert organic solvent, e.g. methylene chloride, at from about 0° C. to room temperature in the presence of a non-nucleophilic base such as triethylamine or diisopropylethylamine. Quaternization or protonation as described above then gives the cationic heterocycle substituent.

For a second procedure, the hydroxyl group of the precursor substituent may be converted into the reactive trifluoromethanesulfonate (triflate) group. However, such an activating group cannot be isolated by conventional techniques but may be formed and used in situ. Thus, treatment of the hydroxyl group with trifluoromethanesulfonic (triflic) anhydride in the presence of a hindered, non-nucleophilic base such as 2,6-lutidine, 2,4,6-collidine, or 2,6-di-tert-butyl-4-methylpyridine in a suitable solvent, such as dichloromethane, at reduced temperatures provides for the generation of the triflate activating group. Alternatively, the iodide described above may be treated in situ with silver trifluoromethanesulfonate in a suitable solvent such as acetonitrile at reduced temperatures to provide for the generation of the triflate activating group. The triflate is then treated as described hereinabove for the iodide.

Where the cationic substitution has a substituent $R^c$, the most facile method of providing such a substituent is to employ as the reactant in the preparation methods described above a nitrogen containing compound which already has the desired substituent. Such substituted compounds are readily available starting materials or may be prepared in a straight-forward manner using known literature methods.

A second suggested synthesis of a cationic heterocycle substituent starting from a precursor substituent such as hydroxymethyl consists of oxidation of the alcohol functionallity to an aldehyde followed by Wittig-type olefination with an appropriate nitrogen-containing aromatic substituted reagent, and finally quaternization. The oxidation may be conveniently accomplished by a Swern oxidation employing oxalyl chloride-dimethylsulfoxide followed by triethylamine. The reaction is conducted in methylene chloride as a solvent at from $-70°$ C. to $0°$ C. The Wittig reaction is carried-out by reacting the aldehyde with the desired Wittig reagent in a polar solvent such as acetonitrile or dimethylsulfoxide at about room temperature. Suitable Wittig reagents include: pyridylmethylenetriphenylphosphorane, quinolylmethylenetriphenylphosphorane, thiazolylmethylenetriphenylphosphorane, and N-methyltetrazolymethylenetriphenylphosphorane. Quaternization or protonation as described above then completes the synthesis of the cationic heterocycle substituent.

A third suggested synthesis of a cationic heterocycle substituent starting from a precursor substituent such as hydroxymethyl consists of treatment of the precursor with dicyclohexylcarbodiimide in the presence of a aromatic heterocycle carboxylic acid, such as nicotinic acid. The reaction is conducted in a polar solvent, such as pyridine, and an organic nitrogen base, such as dimethylaminopyridine, is also present. The reaction is typically conducted at room temperature. Depending on the particular heterocycle substituent that is desired, many other synthesis schemes may be employed, as would be apparent to an organic chemist skilled in the art.

The steps for preparing the 2-phenyl carbapenem intermediate are well known in the art and are explained in ample detail in U.S. Pat. Nos. 4,260,627 and 4,543,257.

In the preparation methods described above, the carboxyl group at the 3-position remains blocked by a carboxyl covering group until the final product is prepared. Then, if the anionic carboxylate is desired so as to form a zwitterionic internal salt, deblocking may be carried out in a conventional manner, with care being taken to avoid a procedure which is so harsh as to disrupt other portions of the final product molecule.

The general synthesis description above and the particular exemplifications which follow show the 6-(1-hydroxyethyl) moiety, which is preferred in most cases. However, it has been found that with certain 2-sidechain selections, the ultimate balance of favorable biological properties in the overall molecule may be enhanced by selection of the 6-(1-fluoroethyl) moiety instead. Preparation of this and other 6-fluoroalkyl compounds within the scope of the present invention may be carried out in a straightforward manner using techniques well know in the art of preparing carbapenem antibacterial compounds. See, e.g., J. G. deVries et al., Heterocycles, 23 (8), 1915 (1985); BE 900 718 A (Sandoz).

The invention is further defined by reference to the following examples, which are intended to be illustrative and not limiting. All temperatures are in degrees Celsius.

EXAMPLE 1

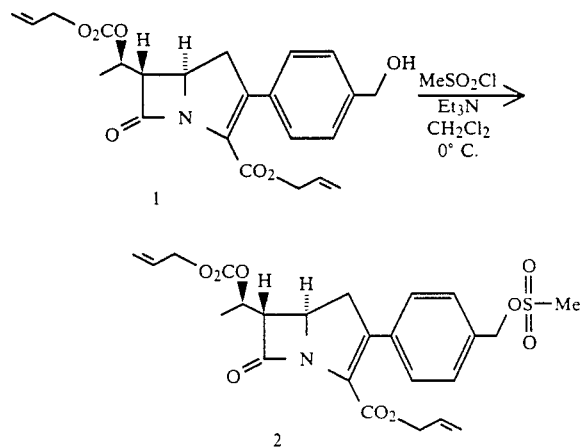

Allyl-(5R, 6S)-2-(4-methanesulfonyloxymethylphenyl)-6-[1R-(allyloxycarbonyloxy)ethyl]carbapen-2-em-3-carboxylate (2)

To a stirred solution of 42.7 mg (0.1 mmole) of (1) in 1 ml of sieve dried $CH_2Cl_2$ at $0°$ C. under a nitrogen atmosphere was added sequentially 15.2 mg (0.15 mmole) of neat $Et_3N$ and then 14.9 mg (0.13 mmole) of neat mesyl chloride. The resulting mixture was stirred for 15 minutes, and then partitioned between EtOAc, ice-$H_2O$, and some 2N HCl. The organic phase was separated, washed with saturated NaCl solution, dried over $Na_2SO_4$, filtered, evaporated, and dried in vacuo to give a quantitative yield of (2);

$^1$H—NMR (200 MHz, $CDCl_3$): $\delta$1.49 (d, J=6.4 Hz, $CH_3CH$), 2.96 (s, $CH_3SO_3$), 3.18 (dd, J=9.9, 18.1 Hz, H-1), 3.34 (dd, J=8.9, 18.1 Hz, H-1), 3.43 (dd, J=2.8, 8.1 Hz, H-6), 4.30 (dt, J=2.3, 2.8, 9.9 Hz, H-5), 4.66 (m, $CH_3CHOH$ and $CH_2CH=CH_2$), 5.26 (m, $OCH_2CH=CH_2$), 5.29 (s, $ArCH_2OSO_2$), 7.40 ppm (s, Ar-H); IR ($CH_2Cl_2$): 1780, 1745, 1725 cm$^{-1}$; UV (p-Dioxane): $\lambda_{max}$=314 nm.

EXAMPLE 2

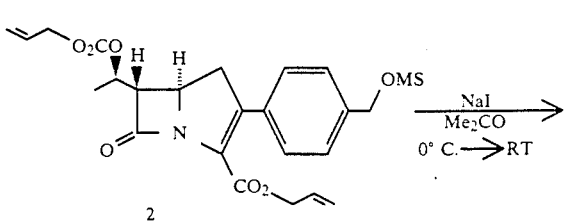

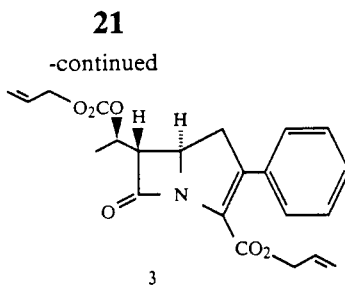

Allyl-(5R, 6S)-2-(4-iodomethylphenyl)-6-[1R-(allyloxycarbonyloxy)ethyl]-carbapen-2-em-3-carboxylate (3)

To a stirred solution of 38.8 mg (0.077 mmole) of (2) in 1 ml of acetone at 0° C. was added all at once 23 mg (0.15 mmole) of NaI. The ice-H₂O bath was removed and the mixture stirred further under a nitrogen atmosphere for 0.5 hour. After this time, the resulting mixture was partitioned between EtOAc, ice-H₂O, 5% Na₂S₂O₄ (aq.) solution and saturated NaCl solution. The organic phase was separated, dried over Na₂SO₄, filtered, evaporated and dried in vacuo to give (3);

¹H—NMR (200 MHz, CDCl₃): δ1.49 (d, J=7.4 Hz, CH₃), 3.17 (dd, J=9.8, 18.1 Hz, H-1), 3.29 (dd, J=8.7, 18.1 Hz, H-1), 3.41 (dd, J=2.9, 8.7 Hz, H-6), 4.27 (dt, J=2.9, 8.7, 9.8 Hz, H-5), 4.65 (m, CH₃CHOH and OCH₂CH=CH₂), 5.26 (m, OCH₂CH=CH₂), 5.89 (m, OCH₂CH=CH₂), 7.32 ppm (m, Ar-H). IR (CH₂Cl₂): 1780, 1745, 1725 cm⁻¹; UV(p-Dioxane): λ$_{max}$=322 nm.

EXAMPLE 3

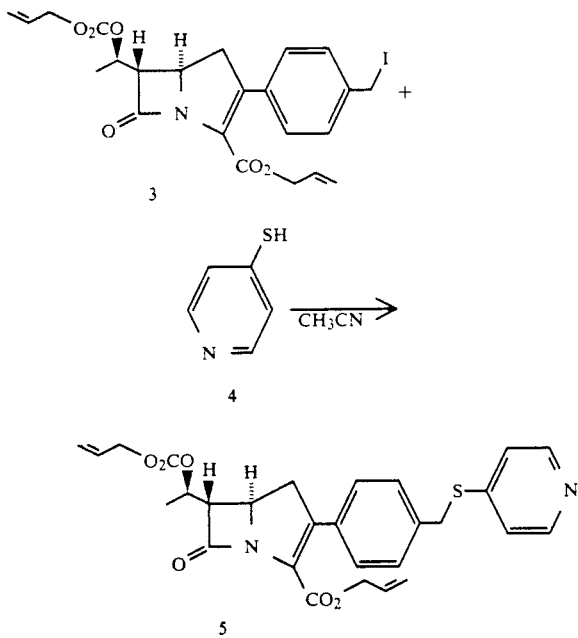

Allyl-(5R, 6S)-2-[4-(4'-pyridylthiomethyl)phenyl]-6-[1R-(allyloxycarbonyloxy)ethyl]carbapen-2-em-3-carboxylate (5)

In 1.2 ml of acetonitrile (CH₃CN) at 0° there was dissolved 34 mg (0.30 mmole) of 4-mercaptopyridine (4), followed by 34 μl (0.195 mmol) of diisopropylethylamine (i-Pr₂NEt). The reaction mixture was stirred for 40 minutes, after which the product was purified by thin layer chromatography (2-1000μ plates) eluting with 50% ethyl acetate/hexane. A UV band near the origin was isolated and washed with ethyl acetate and evaporated to give 54 mg of a yellowish oil (0.103 mmol, 56%).

¹H—NMR (200 MHz, CDCl₃): δ1.50 (d, 3H), 3.25 (m, 2H), 3.33 (dd, 1H), 4.23 (s, 2H), 4.30 (dt, 1H), 4.67 (m, 5H), 5.27 (m, 4H), 5.90 (m, 2H), 7.15 (d, 2H), 7.40 (d, 2H), 8.42 ppm (d, 2H).

EXAMPLE 4

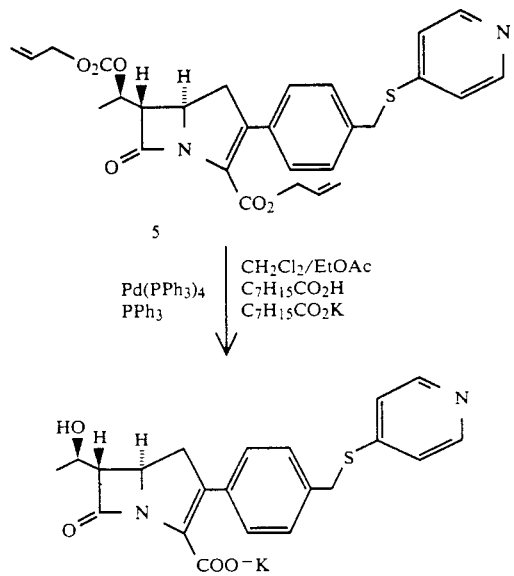

Potassium (5R, 6S)-2-[4-(4'-pyridylthiomethyl)phenyl]-6-[1R-hydroxyethyl]carbapen-2-em-3-carboxylate (6)

In 1.8 ml of sieve dried dichloromethane (CH₂Cl₂) and 1.8 ml of ethyl acetate (EtOAc) there was dissolved 54 mg (0.10 mmol) of the crude product of Example 3, carbapenem (5), after which there was added 7.4 mg of triphenylphosphine and 9.6 mg of tetrakis(triphenylphosphine)palladium. Next there was added 218 μl (0.10 mmol) of 0.5M potassium 2-ethylhexanoate in ethyl acetate and 17 μl (0.10 mmol) of 2-ethylhexanoic acid, and the reaction mixture was stirred at room temperature under a nitrogen atmosphere for 1 hour, 40 minutes. Much precipitate formed; and the reaction mixture was centrifuged, after which the solvent was blown down with nitrogen and the residue was extracted three times with ethyl ether (Et₂O), with centrifuging each time to extract solvent from the solid pellet. The pellet was then dissolved in 3.5 ml of water and extracted with ethyl acetate, followed by centrifuging to separate the organic and aqueous layers. The aqueous layer still had undissolved precipitate and consequently was filtered through a 0.22μ material, washing with water, after which it was evaporated and lyophilized. There was obtained 42.1 mg of off-white fluffy solid.

¹H—NMR (200 MHz, D₂O): δ1.35 (d, 3H), 3.04 (dd, 1H), 3.42 (dd, 1H), 3.54 (m, 1H), 4.32 (m, 2H), 4.36 (s, 2H), 7.40 (m, 6H), 8.28 ppm (d, 2H). UV(H₂O): λ$_{max}$=278, 302 nm.

EXAMPLES 5-8

Employing the procedures described above, additional compounds of the present invention were prepared. These are described in the table below, which additionally includes characterizing data and the method of preparation for each compound.

| Example No. | Z | $\lambda_{max}^{H_2O}$ (nm) |
|---|---|---|
| 5 | (N-ethyl-N-methylamino)-2-pyridyl | 299 |
| 6 | 2-(ethylthio)pyridyl | 299 |
| 7 | 3-(ethylthio)pyridyl | 300 |
| 8 | 2-(ethylthiomethyl)pyridyl | 263, 306 |

EXAMPLE 9

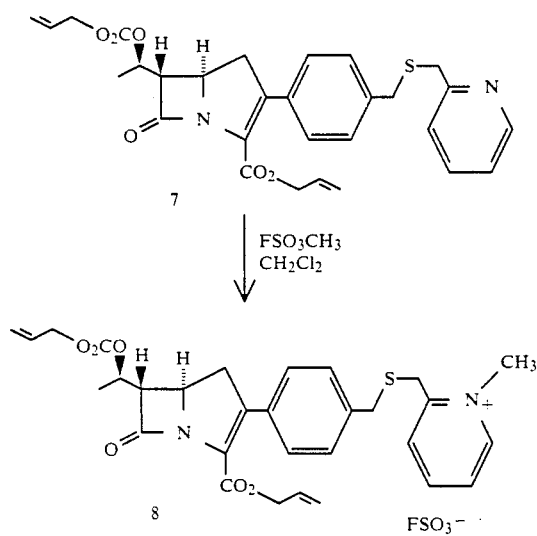

Allyl-(5R, 6S)-2-(4-[2-(N-methylpyridiniummethylthio)methyl]-phenyl)-6-[1R-(allyloxycarbonyloxy)ethyl]carbapen-2-em-3-carboxylate fluorosulfonate (8)

In 2.0 mL of sieve dried CH$_2$Cl$_2$ at room temperature there was dissolved 77 mg (0.144 mmol) of 2-(2-pyridyl-methylthiomethyl-4-phenyl)carbapenem 7 (prepared by the procedure described in Example 3), after which there was added 18 μl (0.222 mmol) of methylfluorosulfonate. The solution was stirred at room temperature for 1.5 hours and then the solvent was removed under a stream of nitrogen. The residue was dried under vacuum to provide carbapenem 8 as yellow foam.

$^1$H—NMR (200 MHz, DMSO-d6): δ1.36 (d, 3H), 3.10–3.90 (m, 5H), 3.46 (br s, 3H), 4.30 (s, 2H), 4.61 (m, 5H), 5.18 (m, 4H), 5.90 (m, 2H), 7.23 (d, 2H), 7.30 (m, 2H), 7.98 (d, 2H), 8.44 (br t, 1H), 8.92 ppm (d, 1H).

EXAMPLE 10

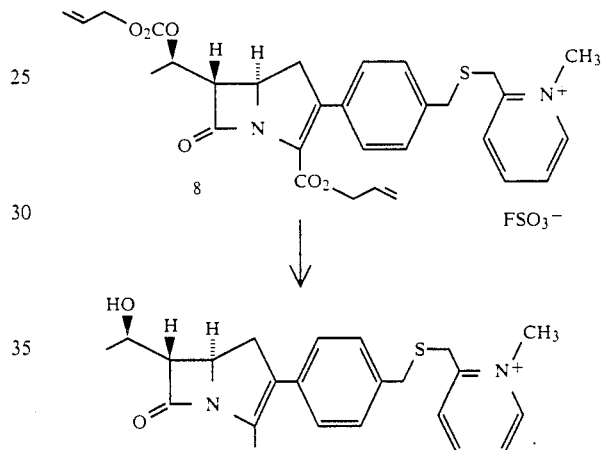

(5R, 6S)-2-(4-[2-(N-Methylpyridiniummethylthio)methyl]-phenyl)-6-[1R-hydroxyethyl]carbapen-2-em-3-carboxylate fluorosulfonate (9)

The crude product of Example 9, carbapenem (8) was dissolved in 2.1 ml of sieve dried dichloromethane (CH$_2$Cl$_2$) and 1.8 ml of ethyl acetate (EtOAc), after which there was added 10.4 mg of triphenylphosphine and 13.4 mg of tetrakis(triphenylphosphine)palladium. 0.5M Potassium 2-ethylhexanoate in ethyl acetate (218 μl, 0.10 mmol) was then added, followed by 2-ethylhexanoic acid (17 μl, 0.10 mmol), and the reaction mixture was stirred at room temperature under a nitrogen atmosphere for 1 hour, 25 minutes. The solution remained cloudy throughout the reaction. The reaction mixture was transferred to a centrifuge tube and the solvent was blown down with nitrogen and the residue was extracted four times with ethyl ether (Et$_2$O), with centrifuging each time to extract solvent from the solid pellet. The pellet was then dissolved in 7.0 ml of water and extracted with ethyl acetate, followed by centrifuging to separate the organic and aqueous layers. The aqueous layer was concentrated under vacuum and the concentrated solution purified by reverse phase TLC (4:1, water:ethanol) to provide 25.6 mg of the title compound as a pale yellow fluffy solid.

$^1H$—NMR (300 MHz, $D_2O$): δ1.30 (d, 3H), 3.05 (dd, 1H), 3.38 (dd, 1H), 3.50 (dd, 1H), 3.80 (s, 2H), 4.04 (m, 1H), 4.12 (s, 2H), 4.22 (s, 3H), 4.22 (m, 2H), 7.05–7.46 (m, 4H), 7.70 (d, 2H), 8.20 (t, 1H), 8.56 ppm (d, 1H). UV($H_2O$): $\lambda_{max}$=270, 303 nm.

EXAMPLE 11

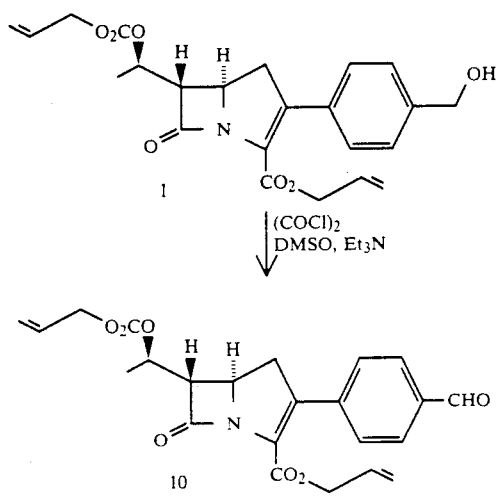

Allyl-(5R, 6S)-2-(4-formylphenyl)-6-[1R-(allyloxycarbonyloxy)ethyl]carbapen-2-em-3-carboxylate (10)

To a solution of 25 μl (0.28 mmol) of oxalyl chloride in 620 μl of $CH_2Cl_2$ at −50° C. was added a solution of 40.8 μl (0.57 mmol) of dimethylsulfoxide (DMSO) in 120 μl of $CH_2Cl_2$. The solution was stirred 10 mm at −50° C. and then a solution of 100 mg (0.234 mmol) of carbapenem 1 in 1.15 mL of $CH_2Cl_2$ was added dropwise over a 15 minute period. Triethylamine (184 μl, 1.32 mmol) was then added and the reaction solution was warmed to room temperature and diluted with ice water. The mixture was acidified to pH 4.0 with 1.0N aqueous HCl and the mixture extracted with $CH_2Cl_2$. The organic layer was separated and washed with 5% aqueous sodium bicarbonate, followed by water and brine. The organic layer was then dried over magnesium sulfate, filtered and concentrated under vacuum. The residue was purified by thin layer chromatography (silica gel, 1:1; EtOAc:hexanes) to provide the formylphenyl carbapenem 10.

$^1H$—NMR (200 MHz, $CDCl_3$): δ1.39 (d, 3H), 3.19 (m, 2H), 3.38 (dd, 1H), 4.25 (dt, 1H), 4.57 (m, 5H), 5.19 (m, 4H), 5.79 (m, 2H), 7.41 (d, 2H), 7.78 (d, 2H), 9.91 ppm (s, 1H).

EXAMPLE 12

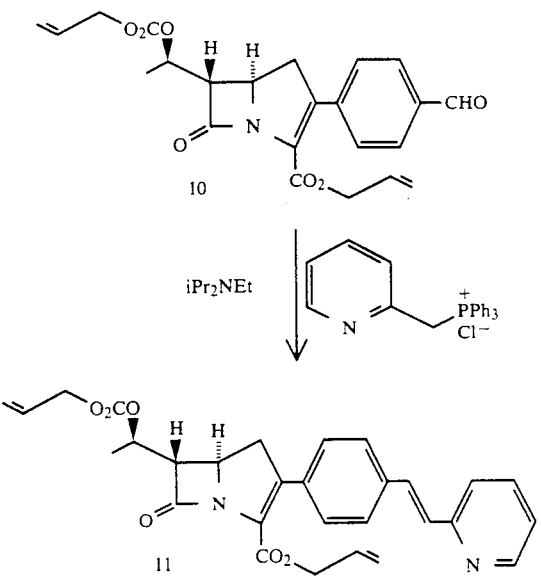

Allyl-(5R, 6S)-2-(4-[E-(2-pyridyl)vinyl]phenyl)-6-[1R-(allyloxycarbonyloxy)ethyl]carbapen-2-em-3-carboxylate (11)

To a solution of 51 mg (0.12 mmol) of carbapenem 10 in 510 μl of DMSO was added 155.9 mg (0.36 mmol) of (2-pyridylmethyl) triphenyl phosphonium chloride followed by 64.5 μl (0.36 mmol) of diisopropylethylamine. The mixture was stirred 2.5 hours at room temperature and then diluted with ethyl acetate. Thin layer chromatography of the solution provided 48 mg of the pyridylvinyl phenyl carbapenem 11.

$^1H$—NMR (200 MHz, $CDCl_3$): δ1.48 (d, 3H), 3.27 (m, 2H), 3.43 (dd, 1H), 4.28 (dt, 1H), 4.66 (m, 5H), 5.26 (m, 4H), 5.90 (m, 2H), 7.14–7.74 (m, 9H), 8.60 ppm (br d, 1H).

EXAMPLE 13

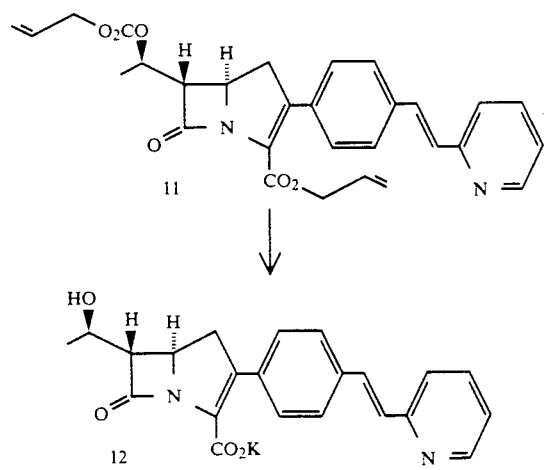

Potassium (5R, 6S)-2-(4-[E-(2-pyridyl)vinyl]phenyl)-6-[1R-hydroxyethyl]carbapen-2-em-3-carboxylate (12)

The product of Example 12, 2-(2-pyridyl-2-vinyl-4-phenyl)carbapenem (11) (12.7 mg, 0.025 mmol) was dissolved in 0.38 ml of sieve dried dichloromethane ($CH_2Cl_2$) and 0.38 ml of ethyl acetate (EtOAc), after which there was added 2.62 mg of triphenylphosphine and 2.3 mg of tetrakis(triphenylphosphine)palladium. 0.5M Potassium 2-ethylhexanoate in ethyl acetate (50 μl, 0.025 mmol) was then added, followed by 2-ethylhexanoic acid (4 μl, 0.10 mmol), and the reaction mixture was stirred at room temperature under a nitrogen atmosphere for 2 hours. The solution remained cloudy throughout the reaction. The reaction mixture was transferred to a centrifuge tube and the solvent was blown down with nitrogen and the residue was extracted four times with ethyl ether ($Et_2O$), with centrifuging each time to extract solvent from the solid pellet. The pellet was then dissolved in 4.0 ml of water and extracted with ethyl acetate, followed by centrifuging to separate the organic and aqueous layers. The aqueous layer was concentrated under vacuum and lyophilized to provide 5.0 mg of the title compound as a pale yellow fluffy solid.

$^1$H—NMR (200 MHz, $D_2O$): δ1.36 (d, 3H), 3.09 (dd, 1H), 3.44 (dd, 1H), 3.55 (dd, 1H), 4.30 (m, 2H), 7.18–7.95 (m, 9H), 8.50 ppm (br s, 1H). UV($H_2O$): $\lambda_{max}$=342 nm.

EXAMPLE 14

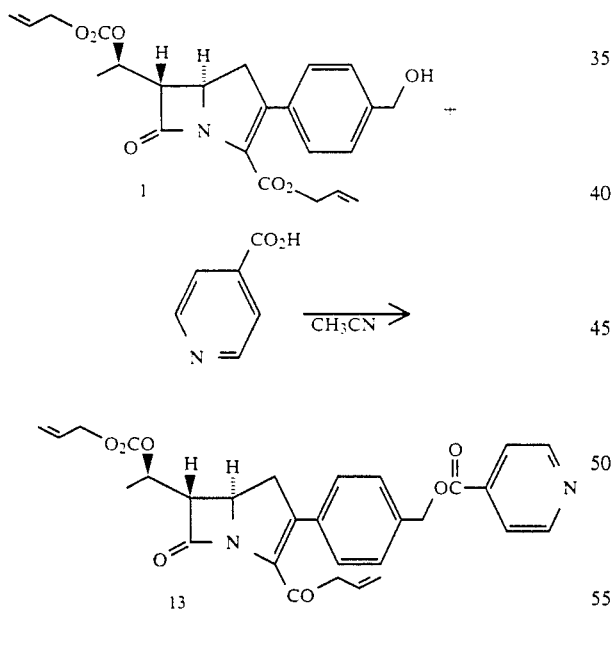

Allyl-(5R, 6S)-2-(4-[4'-pyridylcarbonyloxymethyl]phenyl)-6-[1R-(allyloxycarbonyloxy)ethyl]carbapen-2-em-3-carboxylate (13)

To a solution of 128 mg (0.30 mmol) of (1) and 52 mg (0.42 mmol) of isonicotinic acid in 2.5 mL of pyridine was added 89 mg (0.432 mmol) of dicyclohexylcarbodiimide and 12 mg (0.098 mmol) of 4-N,N-dimethylaminopyridine. The solution became cloudy after 40 minutes. After the reaction was stirred a total of 3 hours, the mixture was filtered and the filtrate concentrated under vacuum. The residue was partitioned between 20 mL 1:1 ether-$CH_2Cl_2$ and 10 mL of 5% aqueous sodium sulfite solution. The layers were separated and the organic phase was washed with 5% aqueous sodium sulfite solution and then with brine. The organic phase was then dried over magnesium sulfate and filtered. The filtrate was concentrated under vacuum and the residue was dissolved in ethyl acetate and this solution was filtered. The filtrate was concentrated and the residue was purified by plate layer chromatography (silica gel; 7:3 ethyl acetate-hexanes) to provide 73 mg of the pyridylcarbonyloxymethyl carbapenem 13.

$^1$H—NMR (200 MHz, $CDCl_3$): δ1.5 (d, $CH_3$), 3.3 (q, 2H), 3.5 (dd, 1H), 4.3 (dt, 1H), 4.7 (m, 4H), 5.3 (m, 7H), 5.9 (m, 2H), 7.45 (m, 4H), 7.9 (d, 2H), 8.8 ppm (broad s, 2H).

EXAMPLE 15

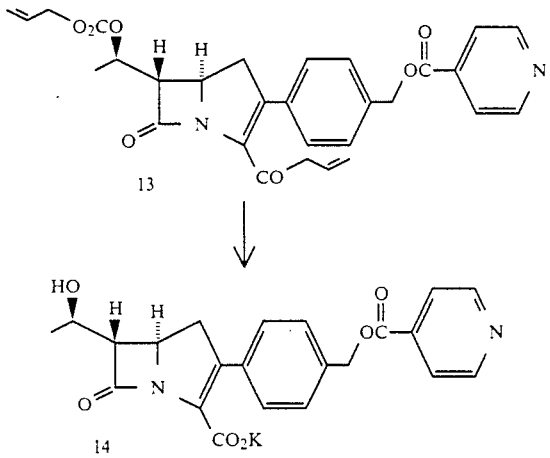

Potassium (5R, 6S)-2-(4-[4'-pyridylcarbonyloxymethyl]phenyl)-6-(1R-hydroxyethyl)carbapen-2-em-3-carboxylate (14)

In a manner analogous to that described in Example 13, but starting with the carbapenem 13, carbapenem 14 was prepared.

$^1$H—NMR (200 MHz, $D_2O$): δ1.5 (d, $CH_3$), 3.2 (q, 1H), 3.6 (m, 2H), 4.4 (m, 2H), 5.5 (s, 2H), 7.5 (broad q, 6H), 8.1 ppm (broad s, 2H). UV($H_2O$): $\lambda_{max}$=300 nm.

What is claimed is:

1. A compound of the formula I:

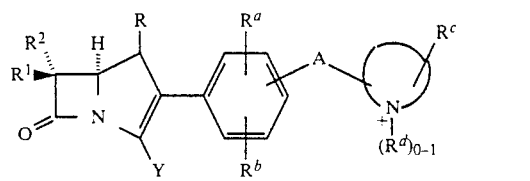

wherein:
R is H or $CH_3$;
$R^1$ and $R^2$ are independently H, $CH_3$—, $CH_3CH_2$—, $(CH_3)_2CH$—, $HOCH_2$—, (R)—$CH_3CH(OH)$—, $(CH_3)_2C(OH)$—, $FCH_2$—, $F_2CH$—, $F_3C$—, (R)—$CH_3CH(F)$—, $CH_3CF_2$—, or $(CH_3)_2C(F)$—;
$R^a$ and $R^b$ are independently hydrogen or:
a) a trifluoromethyl group: —$CF_3$;
b) a halogen atom: —Br, —Cl, —F, or —I;

c) $C_1$-$C_4$ alkoxy radical: —$OC_{1-4}$ alkyl, wherein the alkyl is optionally mono-substituted by $R^q$, where $R^q$ is a member selected from the group consisting of —OH, —$OCH_3$, —CN, —$C(O)NH_2$, —OC-$(O)NH_2$, CHO, —$OC(O)N(CH_3)_2$, —$SO_2NH_2$, —$SO_2N(CH_3)_2$, —$SOCH_3$, —$SO_2CH_3$, —F, —$CF_3$, —$COOM^a$ (where $M^a$ is hydrogen, alkali metal, methyl or phenyl), tetrazolyl (where the point of attachment is the carbon atom of the tetrazole ring and one of the nitrogen atoms is mono-substituted by $M^a$ as defined above) and —$SO_3M^b$ (where $M^b$ is hydrogen or an alkali metal);

d) a hydroxy group: —OH;

e) a carbonyloxy radical: —O(C=O)$R^s$, where $R^s$ is $C_{1-4}$ alkyl or phenyl, each of which is optionally mono-substituted by $R^q$ as defined above;

f) a carbamoyloxy radical: —O(C=O)N($R^y$)$R^z$ where $R^y$ and $R^z$ are independently H, $C_{1-4}$ alkyl (optionally mono-substituted by $R^q$ as defined above), together a 3- to 5-membered alkylidene radical to form a ring (optionally substituted with $R^q$ as defined above) or together a 2- to 4-membered alkylidene radical, interrupted by —O—, —S—, —S(O)—, —S(O)$_2$— or —$NR^e$—, to form a ring (where $R^e$ is hydrogen, $C_1$-$C_4$alkyl, and $C_1$-$C_4$alkyl mono-substituted with $R^q$ and the ring is optionally mono-substituted with $R^q$ as defined above);

g) a sulfur radical: —S(O)$_n$—$R^s$ where n=0-2, and $R^s$ is defined above;

h) a sulfamoyl group: —$SO_2N(R^y)R^z$ where $R^y$ and $R^z$ are as defined above;

i) azido: $N_3$ j) a formamido group: —N($R^t$)(C=O)H, where $R^t$ is H or $C_{1-4}$ alkyl, and the alkyl thereof is optionally mono-substituted by $R^q$ as defined above;

k) a ($C_1$-$C_4$ alkyl)carbonylamino radical: —N($R^t$)(C=O)$C_{1-4}$ alkyl, where $R^t$ is as defined above, and the alkyl group is also optionally mono-substituted by $R^q$ as defined above;

l) a ($C_1$-$C_4$ alkoxy) carbonylamino radical: —N($R^t$)(C=O)O$C_{1-4}$ alkyl, where $R^t$ is as defined above, and the alkyl group is also optionally mono-substituted by $R^q$ as defined above;

m) a ureido group: —N($R^t$)(C=O)N($R^y$)$R^z$ where $R^t$, $R^y$ and $R^z$ are as defined above;

n) a sulfonamido group: —N($R^t$)$SO_2R^s$, where $R^s$ and $R^t$ are as defined above;

o) a cyano group: —CN;

p) a formyl or acetalized formyl radical: —(C=O)H or —CH(OCH$_3$)$_2$;

q) ($C_1$-$C_4$ alkyl)carbonyl radical wherein the carbonyl is acetalized: —C(OCH$_3$)$_2C_{1-4}$ alkyl, where the alkyl is optionally mono-substituted by $R^q$ as defined above;

r) carbonyl radical: —(C=O)$R^s$, where $R^s$ is as defined above;

s) a hydroximinomethyl radical in which the oxygen or carbon atom is optionally substituted by a $C_1$-$C_4$ alkyl group: —(C=NO$R^z$)$R^y$ where $R^y$ and $R^z$ are as defined above, except they may not be joined together to form a ring;

t) a ($C_1$-$C_4$ alkoxy)carbonyl radical: —(C=O)O$C_{1-4}$ alkyl, where the alkyl is optionally mono-substituted by $R^q$ as defined above;

u) a carbamoyl radical: —(C=O)N($R^y$)$R^z$ where $R^y$ and $R^z$ are as defined above;

v) an N-hydroxycarbamoyl or N($C_1$-$C_4$ alkoxy)-carbamoyl radical in which the nitrogen atom may be additionally substituted by a $C_1$-$C_4$ alkyl group: —(C=O)—N(O$R^y$)$R^z$ where $R^y$ and $R^z$ are as defined above, except they may not be joined together to form a ring;

w) a thiocarbamoyl group: —(C=S)N($R^y$)$R^z$ where $R^y$ and $R^z$ are as defined above;

x) carboxyl: —COO$M^b$, where $M^b$ is as defined above;

y) thiocyanate: —SCN;

z) trifluoromethylthio: —$SCF_3$;

aa) tetrazolyl, where the point of attachment is the carbon atom of the tetrazole ring and one of the nitrogen atoms is mono-substituted by hydrogen, an alkali metal or a $C_1$-$C_4$ alkyl optionally substituted by $R^q$ as defined above;

ab) an anionic function selected from the group consisting of: phosphono [P=O(O$M^b$)$_2$]; alkylphosphono {P=O(O$M^b$)—[O($C_1$-$C_4$ alkyl)]}; alkylphosphinyl [P=O(O$M^b$)—($C_1$-$C_4$alkyl)]; phosphoramido [P=O(O$M^b$)N($R^y$)$R^z$ and P=O(O$M^b$)NH$R^x$]; sulfino (SO$_2M^b$); sulfo (SO$_3M^b$); acylsulfonamides selected from the structures CON$M^b$SO$_2R^x$, CON$M^b$SO$_2$N($R^y$)$R^z$, SO$_2$N$M^b$CON($R^y$)$R^z$; and SO$_2$N$M^b$CN, where $R^x$ is phenyl or heteroaryl, where heteroaryl is a monocyclic aromatic hydrocarbon group having 5 or 6 ring atoms, in which a carbon atom is the point of attachment, in which one of the carbon atoms has been replaced by a nitrogen atom, in which one additional carbon atom is optionally replaced by a heteroatom selected from O or S, and in which from 1 to 2 additional carbon atoms are optionally replaced by a nitrogen heteroatom, and where the phenyl and heteroaryl are optionally mono-substituted by $R^q$, as defined above; $M^b$ is as defined above; and $R^y$ and $R^z$ are as defined above;

ac) $C_5$-$C_7$ cycloalkyl group in which one of the carbon atoms in the ring is replaced by a heteroatom selected from O, S, NH or N($C_1$-$C_4$ alkyl) and in which one additional carbon atom may be replaced by NH or N($C_1$-$C_4$ alkyl), and in which at least one carbon atom adjacent to each heteroatom has both of its attached hydrogen atoms replaced by one oxygen thus forming a carbonyl moiety and there are one or two carbonyl moieties present in the ring;

ad) $C_2$-$C_4$ alkenyl radical, optionally mono-substituted by one of the substituents a) to ac) above and phenyl which is optionally substituted by $R^q$ as defined above;

ae) $C_2$-$C_4$ alkynyl radical, optionally mono-substituted by one of the substituents a) to ac) above;

af) $C_1$-$C_4$ alkyl radical;

ag) $C_1$-$C_4$ alkyl mono-substituted by one of the substituents a)-ac) above;

ah) a 2-oxazolidinonyl moiety in which the point of attachment is the nitrogen atom of the oxazolidinone ring, the ring oxygen atom is optionally replace by a heteroatom selected from S and N$R^t$ (where $R^t$ is as defined above) and one of the saturated carbon atoms of the oxazolidinone ring is optionally mono-substituted by one of the substituents a) to ag) above;

$R^c$ is $R^a$ as defined hereinabove, hydrogen, or —NR$^y$R$^z$ (where R$^y$ and R$^z$ are defined hereinabove), but independently selected from R$^a$ and from each other if more than one R$^c$ is present, and is attached to a carbon ring atom or a nitrogen heteroatom the valency of which is not satisfied by the ring bonds;

$R^d$ is hydrogen, NH$_2$, O or C$_1$-C$_4$alkyl (where the alkyl group is optionally mono-substituted with R$^q$ as defined under c above);

is a 5- or 6-membered monocyclic aromatic heterocycle or an 8-, 9- or 10-membered bicyclic aromatic heterocycle, the heterocycle containing a first nitrogen in an aromatic 5- or 6-membered first ring, with said first nitrogen quaternary by virtue of a substituent R$^d$ in addition to the ring bonds thereto, with attachment of the heterocycle to A by way of a carbon atom of a ring, with the first ring containing zero or one of either of the atoms of O or S, with the first ring containing zero to two additional nitrogen atoms, with the first ring optionally fused to a 3- or 4-membered moiety to form the optional second ring, with the moiety containing at least one carbon atom, with the moiety containing zero or one of either of the atoms of O or S, with the moiety containing 0 to 2 nitrogen atoms, and with the moiety being saturated or unsaturated and the second ring aromatic or non-aromatic;

A is (CH$_2$)$_m$—O—(CH$_2$)$_n$, where m is zero to 6 and n is zero to 6 and Q is a covalent bond, O, S, SO, SO$_2$, NH, —SO$_2$NH—, —NHSO$_2$—, —CONH—, —NHCO—, —SO$_2$N(C$_1$-C$_4$alkyl)—, —N(C$_1$-C$_4$alkyl)SO$_2$—, —CON(C$_1$-C$_4$alkyl)—, —N(C$_1$-C$_4$alkyl)CO—, —CH=CH—, —CO—, —OC(O)—, —C(O)O— or N(C$_1$-C$_4$alkyl); provided when m=n=zero that Q is not a covalent bond;

Y is selected from:
  i) COOH or a pharmaceutically acceptable ester or salt thereof,
  ii) COOR$^3$ wherein R$^3$ is a readily removable carboxyl covering group which is not a pharmaceutically acceptable ester,
  iii) COOM wherein M is an alkali metal, or
  iv) COO$^-$;

provided that when Y is other than iv) and a quaternary nitrogen heteroatom is present, a counterion Z$^-$ is provided.

2. The compound of claim 1 wherein R$^1$ is H- and R$^2$ is (R)—CH$_3$CH(OH)— or (R)—CH$_3$CH(F)—.

3. The compound of claim 1 wherein

is:

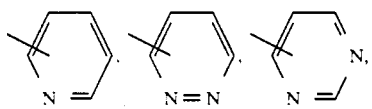

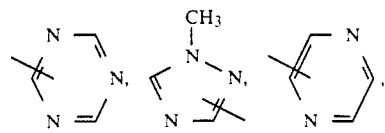

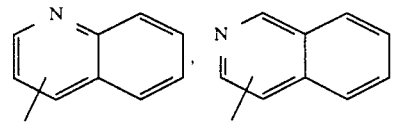

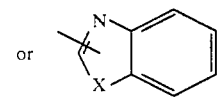

where X=O, S, or NR$_e$;
R$_e$=Me, CH$_2$CN, CH$_2$CONH$_2$, CH$_2$CO$_2^-$, CH$_2$SO$_3^-$.

4. The compound of claim 3 wherein R$^1$ is H- and R$^2$ is (R)—CH$_3$CH(OH)— or (R)—CH$_3$CH(F)—.

5. The compound of claim 1 wherein R$^a$ and R$^b$ are independently selected from:

| | |
|---|---|
| —H | —OCH$_2$CO$_2$Na |
| —OCH$_2$CH$_2$OH | —CF$_3$ |
| —F | —Cl |
| —Br | —I |
| —OH | —OCOCH$_3$ |
| —OCONH$_2$ | —SCH$_3$ |
| —SOCH$_3$ | —SO$_2$CH$_3$ |
| —SCH$_2$CH$_2$OH | —SOCH$_2$CH$_2$OH |
| —SO$_2$NH$_2$ | —SO$_2$N(CH$_3$)$_2$ |
| —NHCHO | —NHCOCH$_3$ |
| —NHCO$_2$CH$_3$ | —NHSO$_2$CH$_3$ |
| —CN | —CHO |
| —COCH$_3$ | —COCH$_2$OH |
| —CH=NOH | —CH=NOCH$_3$ |
| —CH=NOCH$_2$CO$_2$H | —CH=NOCMe$_2$CO$_2$H |
| —CH=NOCMe$_2$CO$_2$Me | —CO$_2$CH$_2$CH$_2$OH |
| —CONH$_2$ | —CONHCH$_3$ |
| —CON(CH$_3$)$_2$ | —CONHCH$_2$CN |
| —CONHCH$_2$CONH$_2$ | —CONHCH$_2$CO$_2$H |
| —CONHOH | —CONHOCH$_3$ |
| -tetrazolyl | —CO$_2$Na |
| —SCF$_3$ | —PO$_3$NaH |
| —CONHSO$_2$Ph | —CONHSO$_2$NH$_2$ |
| —SO$_3$Na | —SO$_2$NHCN |
| —SO$_2$NHCONH$_2$ | —CH=CHCN |
| —CH=CHCONH$_2$ | —CH=CHCO$_2$Na |
| —C≡C—CONH$_2$ | —C≡C—CN |
| —CH$_2$OH | —CH$_2$N$_3$ |
| —CH$_2$CO$_2$Na | —SO$_2$CH$_2$CH$_2$OH |
| —OCH$_3$ or | —CH$_2$I. |

6. The compound of claim 5 wherein R$^1$ is H- and R$^2$ is (R)—CH$_3$CH(OH)— or (R)—CH$_3$CH(F)—.

7. The compound according to claim 1 wherein the compound is

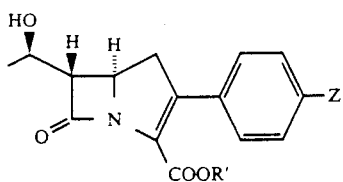

wherein Z is:

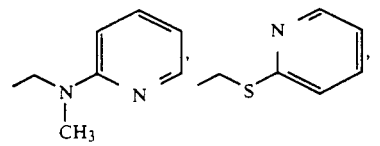

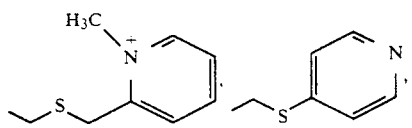

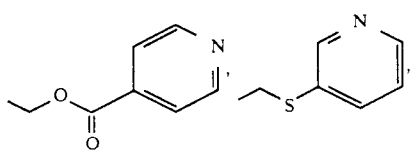

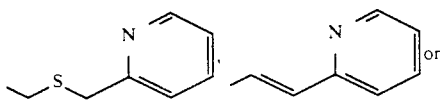

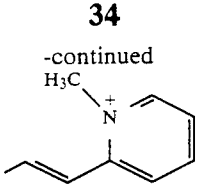

and wherein R' is a negative charge ⁻, an alkali metal, a pharmaceutically acceptable carboxy covering group, or additionally a readily removable carboxyl covering group which is not a pharmaceutically acceptable carboxy covering group.

8. The compound of claim 7 wherein $R^1$ is H- and $R^2$ is (R)—CH$_3$CH(OH)— or (R)—CH$_3$CH(F)—.

9. A pharmaceutical composition for antibacterial use comprising an antibacterially effective amount of a compound of claim 1 and a pharmaceutically acceptable carrier therefor.

10. A method of treating bacterial infections in human or animal subjects in need of such treatment comprising administering to such subject an antibacterially effective amount of a compound of claim 1.

11. A pharmaceutical composition for antibacterial use comprising an antibacterially effective amount of a compound of claim 1, an inhibitorily effective amount of a DHP inhibitor, and, optionally, a pharmaceutically acceptable carrier therefor.

12. The pharmaceutical composition according to claim 11 wherein the DHP inhibitor is 7-(L-2-amino-2-carboxyethylthio)-2-(2,2-dimethylcyclopropanecarboxamide)-2-heptenoic acid.

13. A method of treating bacterial infections in human or animal subjects in need of such treatment comprising coadministering to such subject an antibacterially effective amount of a compound of claim 1 and an inhibitorily effective amount of a DHP inhibitor.

14. The method according to claim 13 wherein the DHP inhibitor is 7-(L-2-amino-2-carboxyethylthio)-2-(2,2-dimethylcyclopropanecarboxamide)-2-heptenoic acid.

* * * * *